(12) United States Patent
Pruckner et al.

(10) Patent No.: US 11,227,203 B2
(45) Date of Patent: Jan. 18, 2022

(54) MEDICAL OR DENTAL INSTRUMENT HAVING AN RFID MEMORY TAG

(71) Applicant: W&H Dentalwerk Bürmoos GmbH, Bürmoos (AT)

(72) Inventors: Christian Pruckner, Vienna (AT); Josef Spitzauer, Loipferding (AT); Michael Reiter, Elsbethen (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 0 days.

(21) Appl. No.: 16/718,115

(22) Filed: Dec. 17, 2019

(65) Prior Publication Data

US 2020/0202191 A1 Jun. 25, 2020

(30) Foreign Application Priority Data

Dec. 20, 2018 (EP) .................................... 18214291

(51) Int. Cl.
   *G06K 19/07* (2006.01)
   *A61B 90/98* (2016.01)
   (Continued)

(52) U.S. Cl.
   CPC .......... *G06K 19/0723* (2013.01); *A61B 90/98* (2016.02); *A61C 3/00* (2013.01);
   (Continued)

(58) Field of Classification Search
   CPC ................................................ G06K 19/0723
   (Continued)

(56) References Cited

U.S. PATENT DOCUMENTS

| 2006/0043198 A1* | 3/2006 | Forster ............. G06K 19/07756 |
| | | 235/492 |
| 2008/0106419 A1* | 5/2008 | Sakama ........... A61B 17/06066 |
| | | 340/572.7 |
| 2010/0219252 A1 | 2/2010 | Kikuchi et al. |

FOREIGN PATENT DOCUMENTS

| JP | 2014-086020 | 5/2014 |
| JP | 2016518212 A | 6/2016 |

(Continued)

OTHER PUBLICATIONS

Search Report for European Application No. 18214291, dated Jun. 11, 2019.

*Primary Examiner* — Rafferty D Kelly
(74) *Attorney, Agent, or Firm* — Klarquist Sparkman, LLP (57) ABSTRACT

A medical or dental instrument having a metal instrument component and an RFID memory tag having a memory chip for storing data, wherein the RFID memory tag is attached to the medical or dental instrument such that the RFID memory tag is electrically connected to the metal instrument component such that the metal instrument component forms an antenna for the RFID memory tag for wireless energy and/or data transfer. An electrically conductive coupling element electrically connects the RFID memory tag to the metal instrument component forming an antenna, the electrically conductive coupling element having a planar first coupling surface on which the RFID memory tag is arranged and a second coupling surface arranged on the metal instrument component forming the antenna. A method for manufacturing or retrofitting a corresponding medical or dental instrument is also described.

20 Claims, 2 Drawing Sheets

(51) Int. Cl.
    *G16H 40/60* (2018.01)
    *A61C 3/00* (2006.01)
    *G06K 19/077* (2006.01)
    *H01Q 1/38* (2006.01)

(52) U.S. Cl.
    CPC ....... *G06K 19/07773* (2013.01); *G16H 40/60* (2018.01); *H01Q 1/38* (2013.01); *A61C 2204/005* (2013.01)

(58) Field of Classification Search
    USPC ....................................................... 235/492
    See application file for complete search history.

(56) References Cited

FOREIGN PATENT DOCUMENTS

| WO | WO2014/017530 | 1/2014 |
| WO | WO2015/149614 | 10/2015 |
| WO | WO2018/167373 | 9/2018 |
| WO | WO2018/195615 | 11/2018 |

\* cited by examiner

MEDICAL OR DENTAL INSTRUMENT HAVING AN RFID MEMORY TAG

CROSS REFERENCE TO RELATED APPLICATION

The present application claims priority from pending European Patent Application No. 18214291.9, filed Dec. 20, 2018, which is incorporated herein by reference.

FIELD

The present invention relates to a medical or dental instrument having an RFID memory tag and a corresponding method for manufacturing or retrofitting such a medical or dental instrument.

DESCRIPTION OF PRIOR ART

Application US 2010/0219252 A1 describes an RFID memory tag having a memory chip that is electrically connected to a metal component of a device, for example a beverage can, such that the metal component serves as an antenna for the RFID memory tag for wireless energy and/or data transfer with a remote reading and/or writing device. This advantageously makes it possible to reduce the dimensions of the RFID memory tag, since the RFID memory tag only requires an antenna smaller than those of conventional RFID memory tags.

SUMMARY

It would be advantageous to improve energy and/or data transfer between the metal component forming the antenna and the RFID memory tag, in particular where the metal component forming the antenna is part of a medical or dental instrument.

According to an embodiment this is achieved by a medical or dental instrument comprising a metal instrument component and an RFID memory tag having a memory chip for storing data, wherein the RFID memory tag is attached to the medical or dental instrument, in particular to the metal instrument component, such that the RFID memory tag is electrically connected to the metal instrument component such that the metal instrument component forms an antenna for the RFID memory tag for wireless energy and/or data transfer with a remote reading and/or writing device. The medical or dental instrument further comprises an electrically conductive coupling element electrically connecting the RFID memory tag to the metal instrument component forming the antenna, wherein the electrically conductive coupling element comprises a substantially planar first coupling surface on which the RFID memory tag is arranged and a second coupling surface arranged on the metal instrument component forming the antenna.

A corresponding method for the manufacture or retrofitting of a medical or dental instrument comprises:
  providing a medical or dental instrument having a metal instrument component,
  providing an RFID memory tag having a memory chip for storing data,
  attaching the RFID memory tag to the medical or dental instrument, in particular to the metal instrument component, through an electrically conductive coupling element, such that the RFID memory tag is electrically connected to the metal instrument component, so that the metal instrument component forms an antenna for the RFID memory tag for wireless energy and/or data transfer to/from a remote reading and/or writing device, wherein the electrically conductive coupling element comprises an essentially planar first coupling surface on which the RFID memory tag is arranged and a second coupling surface.

In practical experiments, the provision of an electrically conductive coupling element having a substantially planar first coupling surface on which the RFID memory tag is arranged and a second coupling surface arranged on the metal instrument component forming an antenna has resulted in improved or excellent energy and/or data transfer. Without being bound to a specific assumption, it can be presumed that the electrically conductive coupling element, in particular the provision of the planar first coupling surface and the second coupling surface, positively influences the energy and/or data transfer based on (lossy) capacitive effects between the RFID memory tag and the metal instrument component. In particular the planar first coupling surface forms in an advantageous way an optimal contact or transmission surface for energy and/or data transfer.

Preferably, the metal instrument component comprises a first bend and the second coupling surface of the electrically conductive coupling element comprises a second bend complementary to the first bend of the metal instrument component, wherein the first bend and the second bend are interlocked to electrically connect the RFID memory tag to the metal instrument component forming an antenna.

The method of manufacturing or retrofitting a medical or dental instrument preferably comprises that the metal instrument component comprises a first bend and the second coupling surface of the electrically conductive coupling element comprises a second bend complementary to the first bend of the metal instrument component, wherein the first bend and the second bend are interlocked to electrically connect the RFID memory tag to the metal instrument component forming an antenna.

Forming the second coupling surface with a second bend having a complementary shape to the first bend of the metal instrument component, advantageously brings about a distinctly improved transfer or coupling of energy and/or data between the RFID memory tag and the curved metal instrument component acting as an antenna, since the second curved coupling surface forms an enlarged contact surface or transfer surface for energy and/or data between the (planar) RFID memory tag and the curved metal instrument component. This is particularly advantageous for medical or dental instruments, which have a large number of curved instrument components. Such an electrically conductive coupling element having a curved second coupling surface also enables, in particular, the simple retrofitting of a medical or dental instrument, during which the RFID memory tag (formed essentially having planar outer sides) can be arranged or fastened, with the aid of the electrically conductive coupling element having a curved second coupling surface, to the curved outer or grip sleeve of the medical or dental instrument. The medical or dental instrument is preferably designed as a straight handpiece or angled handpiece.

Preferably, the first bend and the second bend are/become essentially interlocked without spacing and/or with contact. Preferably, the first bend and the second bend are geometrically complementary to on other, especially in their three-dimensional form. Preferably, the first bend and the second bend are shaped so that one of the two bends is concave and the other of the two bends is convex. These configurations advantageously bring about an additional improvement in energy and/or data transfer.

The medical or dental instrument is in particular designed as an instrument that can be held with one hand. The medical or dental instrument is in particular designed as a diagnosis and/or treatment instrument. The medical or dental instrument preferably comprises at least one of the following elements: a straight or curved or pistol-shaped handpiece; an contra-angle handpiece to which a tool can be attached at an angle to a longitudinal axis of a gripping section; a handle element; an instrument which is provided to emit electromagnetic radiation; an instrument which is provided to emit a fluid; an instrument which is provided to emit a diagnostic and/or therapeutic medium; an instrument which is provided to emit oscillations, in particular ultrasonic oscillations; a motor unit for driving a tool, in particular having a pneumatically or electrically driven motor; an instrument having an image capturing device, in particular having a camera; a coupling element for connection to a media source, in particular a liquid source, a gas source, or a source of electrical energy; an adapter unit.

The RFID memory tag preferably has a (short) antenna section which, in particular (only) by working together with the metal instrument component acting as antenna, achieves a sufficient reading and/or transmitting range for energy and/or data transfer with the remote reading and/or writing device, thereby advantageously reducing the dimensions of the RFID memory tag and thus the space required on or in the medical or dental instrument.

Preferably, the RFID memory tag is a self-contained and/or prefabricated component before being attached to or in the medical or dental instrument. Preferably, the RFID memory tag and the medical or dental instrument represent independent and/or prefabricated units, in particular before the RFID memory tag is attached to the medical or dental instrument. Preferably, the RFID memory tag and the medical or dental instrument form an operative, in particular a communicative, unit after the RFID memory tag has been attached to the medical or dental instrument. The stand-alone, pre-fabricated RFID memory tag advantageously simplifies its mounting or attachment to the medical or dental instrument.

Preferably, the RFID memory tag is/becomes arranged or attached to the medical or dental instrument by at least one of the following means: an adhesive; an molding or injection molding material, in particular plastic; a soldering material; an element that can be mechanically connected to the medical or dental instrument. The mechanical element comprises, for example, a connecting ring on which the RFID memory tag is provided and which can be pushed over a section, for example an end section or coupling section, of the medical or dental instrument. The mechanical element is preferably made of electrically non-conductive material, e.g., plastic or ceramic, in order to prevent an influence on the energy and/or data transfer to or from the RFID memory tag. The above-mentioned means are advantageous in enabling simple and quick attachment and/or retrofitting of the RFID memory tag to the medical or dental instrument.

The data transfer between the RFID memory tag and the remote reading and/or writing device can be unidirectional or bidirectional. The memory chip of the RFID memory tag is thus either designed as a "read-only memory" (ROM memory) from which data can only be read out (unidirectional data transmission), or as a "read-write memory" which can be written to repeatedly and from which data can be read out (bidirectional data transmission).

The metal instrument component, in particular having the first bend, is preferably cylindrical or hollow-cylindrical in shape, the first bend being formed in particular by the curvature of the outer surface of the cylindrical or hollow-cylindrical metal instrument component. Alternatively or additionally, the metal instrument component, in particular having the first bend, is sleeve-shaped or comprises a sleeve of the medical or dental instrument. Preferably, the sleeve-shaped metal instrument component is at least one (metal) section of a grip sleeve or an outer shell or a bearing sleeve for an element, for example a shaft, of the medical or dental instrument or of a coupling sleeve for the detachably connection of the medical or dental instrument to a coupling part, for example to a tool, motor, or adapter. Preferably, the metal instrument component is designed as a tube or pipe. This advantageously makes it possible to use an existing component of the medical or dental instrument as a carrier for the RFID memory tag, especially for retrofitting.

Preferably, the metal instrument component is planar or has a planar surface on which the RFID tag is arranged. The planar metal instrument component is designed, for example, as a wall (or wall segment) inside the medical or dental instrument or as an operating element, preferably as a pushbutton or pressure cover, in particular for actuating a tool-holding device. This advantageously makes it possible to use an existing component of the medical or dental instrument as a carrier for the RFID memory tag, especially for retrofitting.

Preferably, the RFID memory tag is arranged on the outside of the medical or dental instrument, particularly preferably on the outside of the metal instrument component, which in particular has a first bend, in particular on the outside of the grip sleeve or the outer shell. This advantageously makes it simple to attach and/or retrofit the RFID memory label to the medical or dental instrument. Due to its length, the grip sleeve or outer shell can also advantageously be used particularly well as an antenna, thus enabling particularly reliable energy and/or data transfer.

The in particular cylindrical or hollow cylindrical grip sleeve or outer shell is preferably made in one or more parts. The grip sleeve or outer shell is preferably of tubular design and/or has a hollow interior, in particular for holding one or more components, for example parts of the drive device and/or a media, supply, and/or data line of the medical or dental instrument. The grip sleeve or outer shell preferably comprises (along its longitudinal axis) at least two angled (at an angle>0°) or curved sections.

Preferably, the RFID memory tag is located inside the medical or dental instrument, in particular inside a handpiece or contra-angle handpiece, for example on a bearing sleeve for an element of the medical or dental instrument or on a coupling sleeve of the medical or dental instrument. Preferably, the RFID memory tag is located or attached to a component inside the medical or dental instrument. This protects the RFID memory tag particularly well against external influences such as dirt or moisture.

Preferably, the electrically conductive coupling element, at least parts of the RFID memory tag and the metal instrument component forming an antenna form, in particular in an equivalent circuit, an electrical capacitor for capacitive energy and/or data transfer. Accordingly, the method of manufacturing or retrofitting a medical or dental instrument comprises the formation of an electrical capacitor for capacitive energy and/or data transfer by attaching or connecting the electrically conductive coupling element and the RFID memory tag on or to the metal instrument component forming an antenna. The capacitor advantageously allows the wireless transfer of energy and/or data from and/or to the RFID memory tag.

Preferably, the electrically conductive coupling element comprises an electrically conductive adhesive which adhesively, and electrically connects the RFID memory tag to the metal instrument component forming an antenna, in particular inseparably. The RFID memory label is thus in particular glued to the medical or dental instrument, preferably to the metal instrument component. The electrically conductive adhesive preferably comprises at least one polymeric compound and/or at least one organic compound and/or at least one silicone compound. Preferably, electrically conductive particles are provided in and/or dispersed within the electrically conductive adhesive, for example metal particles, in particular copper, silver, or gold particles. Preferably, the electrically conductive adhesive (before forming the adhesive connection between the RFID memory tag and the metal instrument component) is liquid or can be liquefied. Preferably, the electrically conductive adhesive can be cured or cures after the connection is formed between the RFID memory tag and the metal instrument component. Preferably, the first and second, in particular curved, coupling surfaces are formed after application of the electrically conductive adhesive to the RFID memory tag and/or the metal instrument component by contacting or applying the RFID memory tag and the metal instrument component to one another and/or during curing. The use of an electrically conductive adhesive is particularly advantageous as it enables both the electrical connection between the RFID memory tag and the metal instrument component as well as the attachment of the RFID memory tag to the medical or dental instrument.

The electrically conductive coupling element preferably has an electrically conductive shaped element. The electrically conductive shaped element has an essentially planar first coupling surface on which the RFID memory tag is arranged, and a second coupling surface which, in particular, has a second bend complementary to the first bend of the metal instrument component. The electrically conductive shaped element is preferably formed by a completely metallic shaped element or by a carrier material, e.g., plastic or ceramic, having metal particles arranged and/or dispersed therein. The use of a (solid) shaped element as an electrically conductive coupling element advantageously facilitates assembly, in particular the connection of the coupling element to the RFID memory tag and/or to the metal instrument component.

The electrically conductive shaped element preferably is/becomes attached to the medical or dental instrument, in particular to the metal instrument component, using an adhesive. The adhesive comprises either electrically conductive particles (as described above) or it comprises no electrically conductive particles. Alternatively or additionally, the electrically conductive shaped element is attached to the medical or dental instrument, in particular to the metal instrument component, by a cap which surrounds the RFID memory tag and which is described in more detail below. The cap is formed, for example, by molding or injection molding the RFID memory tag, wherein the electrically conductive shaped element is/becomes molded or injection molded with the RFID tag and/or the electrically conductive shaped element is/becomes attached to the cap by molding or injection molding the RFID memory tag. It is also possible to attach the electrically conductive shaped element to the instrument, in particular to the metal instrument component, by clamping it between the cap and the medical or dental instrument or the metal instrument component. The aforementioned attachments advantageously enable a simple and quick assembly of the electrically conductive coupling element, especially together with the RFID memory tag. It is also possible to manufacture the cap as a separate component and only connect the RFID memory tag to the cap when the RFID memory tag is attached to the medical or dental instrument, for example by sliding it in.

Preferably, the electrically conductive coupling element, in particular the electrically conductive shaped element, is plate-shaped and/or has at least one curved surface, in particular a surface having a concave or convex curvature. Preferably, the electrically conductive coupling element, in particular if plate-shaped and/or formed by an adhesive, has two opposing base surfaces which are connected by several side surfaces. Particularly preferably, at least one of the base surfaces is planar, in particular the base surface on which the RFID memory tag is arranged. Particularly preferably, at least one of the base surfaces is curved, in particular that base surface located closer to the metal instrument component or which contacts it. The curvature preferably extends from one of the side surfaces in the direction of a center line of the at least one curved base surface, wherein the wall thickness of the shaped element decreases in the direction of the center line and in particular is lowest in the center. The described form of the electrically conductive coupling element advantageously forms a stable connection between the RFID memory tag and the metal instrument component, thus enabling reliable energy and/or data transfer. In particular, the plate-shaped, electrically conductive coupling element advantageously increases the contact or coupling surface between the RFID memory tag and the metal instrument component, thus improving energy and/or data transfer.

Preferably, the RFID memory tag comprises at least one of the following elements: a carrier for the memory chip, in particular a ceramic carrier; at least one electrical conductor electrically connected to the memory chip, for example a conductive track or an electrically conductive coating; an electrically insulating protective layer; an antenna section comprising in particular the ceramic carrier and the electrical conductor electrically connected to the memory chip. The electrically insulating protective layer preferably surrounds the memory chip, the carrier for the memory chip, and the electrical conductor electrically connected to the memory chip.

The RFID memory tag is preferably disc-shaped, cylindrical, or cuboid in shape. Preferably, the RFID memory tag is configured to transmit data in a frequency range of about 850 MHz-980 MHz or about 2.30 GHz-2.60 GHz.

Preferably, a cap is attached to the medical or dental instrument, in particular to the metal instrument component, which encloses the RFID memory tag. Particularly preferred the cap also contacts and/or encloses the electrically conductive coupling element. The cap is preferably attached to the metal instrument component such that the RFID memory tag and, in particular, also the electrically conductive coupling element are enclosed and that it forms a seal so that the penetration of foreign substances into the RFID memory tag from outside is prevented. The cap is preferably made of an electrically non-conductive material. The cap is preferably made of plastic or ceramic or an adhesive. The cap is formed in particular by molding or injection molding, the RFID memory tag and optionally the electrically conductive coupling element preferably being molded or injection molded with an adhesive or plastic material to produce the cap, wherein the RFID memory tag and optionally the electrically conductive coupling element are particularly preferably fastened to the medical or dental instrument, in particular to the metal instrument component. Preferably the material used to form the cap is liquid before casting or injection and hardens after casting or injection. Preferably, the electrically conductive coupling element and the cap comprise the same adhesive, but only the adhesive of the electrically conductive coupling element comprises electrically conductive particles and/or the adhesive forming the cap does not have electrically conductive particles.

These and other embodiments will be described below with reference to the following drawings.

DETAILED DESCRIPTION

Figures 1, 2:
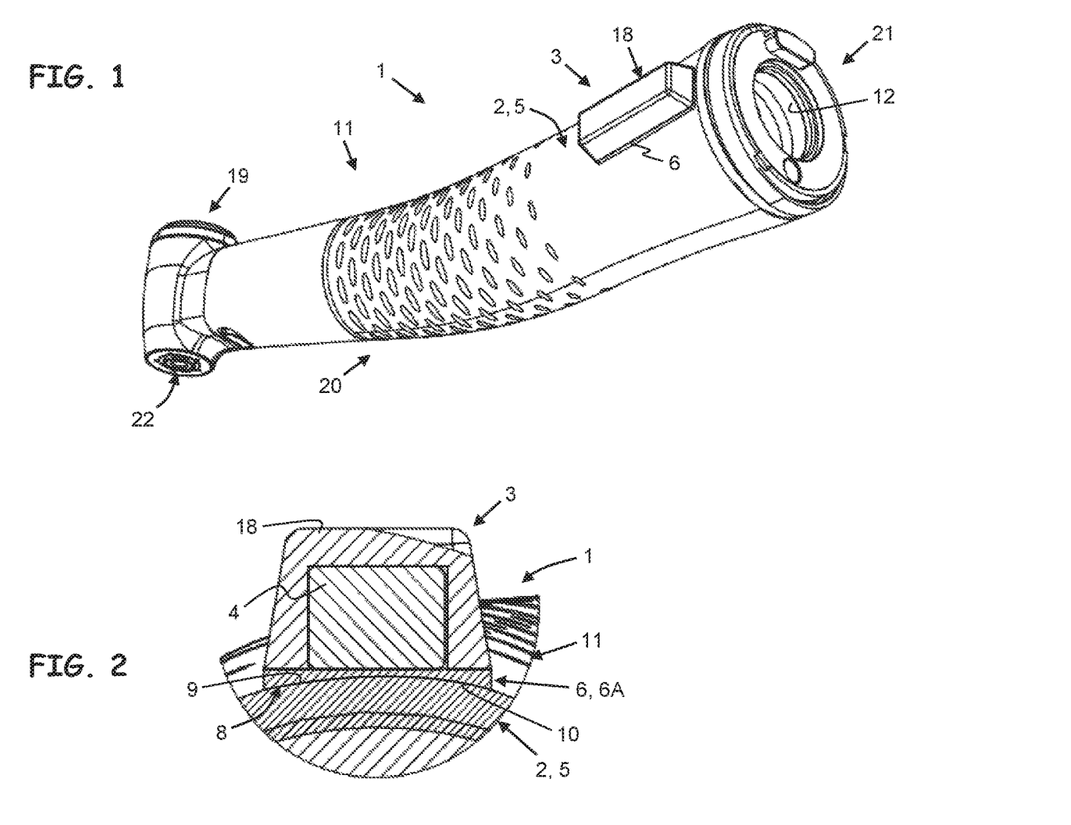
FIG. 1 shows a medical or dental instrument having an RFID memory tag and a metal instrument component that forms an antenna for the RFID memory tag.
FIG. 2 shows a cross-sectional view of an RFID memory tag arranged on a metal instrument component that forms an antenna for the RFID memory tag.
Figure 6:
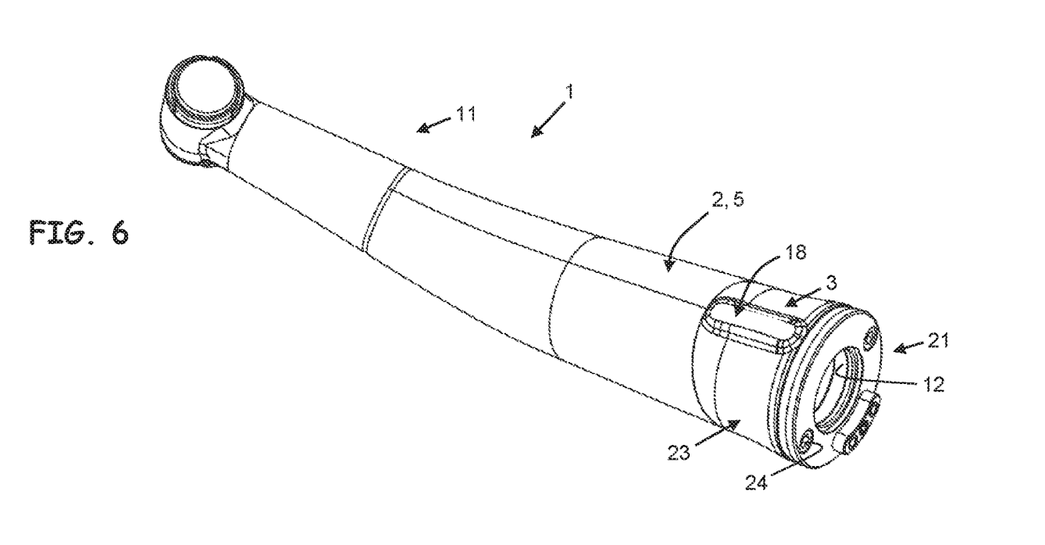
FIG. 6 shows another medical or dental instrument having an RFID memory tag and a metal instrument component that forms an antenna for the RFID memory tag.

FIGS. 1 and 6 each show a medical or dental instrument 1 that is designed as a dental contra-angle handpiece. The contra-angle handpiece 1 comprises a head part 19 and an adjoining curved handle part 20. A tool holder 22 is movably arranged in the head part 19 in order to detachably hold a medical or dental treatment tool. In the head part 19 and/or handle part 20 a drive device is further provided which for example has one or more shafts, a gear, a compressed gas line, an impeller drivable by compressed gas, or the like. The drive device is operatively connected to the tool holder 22 to set it and the tool held therein in motion.

The medical or dental instrument 1 has an outer shell 11 which has a head sleeve part provided on the head part 19 and a bent handle sleeve part provided on the handle part 20.

A coupling device or transmission device 21 is provided at the end of the medical or dental instrument 1 at a position that is remote from the head part 19, which can be detachably connected to a supply unit or dental unit or an external controller (not shown). The coupling device 21 comprises in particular a coupling sleeve 12 for receiving a coupling counterpart, for example a coupling extension, a motor drive, a coupling element, or a supply hose. At least one medium, for example electrical energy, compressed gas, in particular compressed air, water, light, and/or data, for example measurement data, control or regulating data, identification data, for example for identifying a tool, operating data, or similar data, can be transmitted via the coupling device 21. The transmission of at least one medium and/or data between the medical or dental instrument 1 and the supply unit or dental unit or the external controller may be unidirectional or bidirectional.

Furthermore, an RFID memory tag 3 having a memory chip 4 for storing data is provided on the medical or dental instrument 1. The RFID memory tag 3 is attached to the contra-angle handpiece 1 such that the RFID memory tag 3 is electrically connected to a metal instrument component 2 so that the metal instrument component 2 forms an antenna 5 for the RFID memory tag 3 for wireless transfer of energy and/or data to/from a remote reading and/or writing device. The metal instrument component 2, which acts as an antenna 5, is formed by at least one (metal) part of the outer shell 11, in particular by at least one portion of the grip sleeve part of the handle part 20.

An electrically conductive coupling element 6 is provided to electrically connect the RFID memory tag 3 to the metal instrument component 2 forming an antenna 5, i.e., at least a portion of the outer shell 11. As can be seen in particular in FIGS. 2-5, the electrically conductive coupling element 6 comprises an essentially planar first coupling surface 7 on which the RFID memory tag 3 is arranged, and a second coupling surface 8 which is arranged on the metal instrument component 2 (at least part of the outer shell 11) forming an antenna 5.

Figure 5:
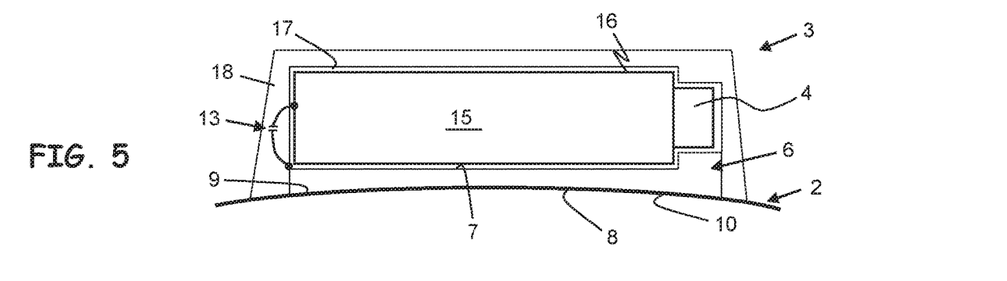
FIG. 5 shows a schematic representation of an RFID memory tag that is connected via an electrically conductive coupling element to a metal instrument component forming an antenna.
Figure 7A:
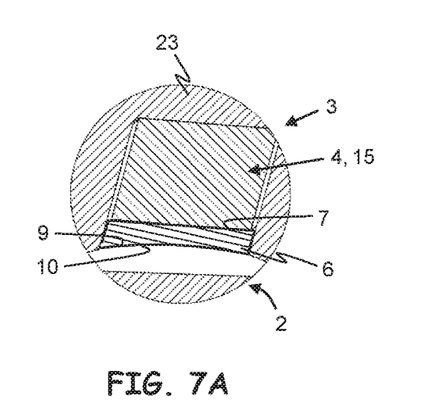
FIG. 7A shows another cross-sectional view of an RFID memory tag arranged on a metal instrument component that forms an antenna for the RFID memory tag.

According to one embodiment, in particular shown in FIGS. 2, 5, and 7A, the metal instrument component 2, for example a section of the outer shell 11, has a first bend 9 and the second coupling surface 8 of the electrically conductive coupling element 6 has a second bend 10 complementary to the first bend 9 of the metal instrument component 2, wherein the first bend 9 and the second bend 10 are interlocked to electrically connect the RFID memory tag 3 to the metal instrument component 2 forming an antenna 5. The connection or contact between the first bend 9 and the second bend 10 extends in particular over the entire second bend 10 of the second coupling surface 8 and is preferably continuous and/or non-spaced. According to FIGS. 2, 5, and 7A, the first bend is 9 convex and the second bend 10 concave, but other shapes are also possible.

The electrically conductive coupling element 6 shown in FIG. 2 comprises an electrically conductive adhesive 6A which adheres and electrically connects the RFID memory tag 3 to the metal instrument component 2, 11 forming an antenna 5. The RFID memory tag 3 is thus glued in particular to the medical or dental instrument 1, preferably the outer shell 11. In addition to the advantage already described of improved energy and/or data transfer between the RFID memory tag 3 and the metal instrument component 2, 11 forming an antenna 5 due to the enlarged coupling surface, the use of the electrically conductive adhesive 6A also makes it possible to attach the RFID memory tag 3 particularly easily and cost-effectively to the medical or dental instrument 1, in particular to the metal outer shell 11 or a metal section of the outer shell 11. This makes simple retrofitting (and a simple method for retrofitting) of a medical or dental instrument 1 possible by affixing the RFID memory tag 3 to the medical or dental instrument 1, in particular to the outer shell 11. The electrically conductive adhesive 6A in particular comprises electrically conductive particles (not shown).

Figure 3:
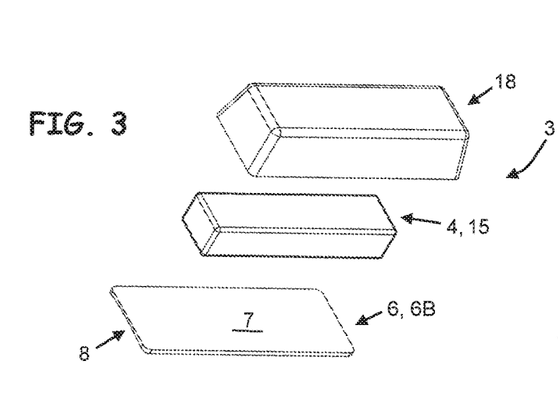
FIG. 3 shows main components of an RFID memory tag, including an electrically conductive coupling element for electrically connecting the RFID memory tag to a metal instrument component forming an antenna.
Figure 4:
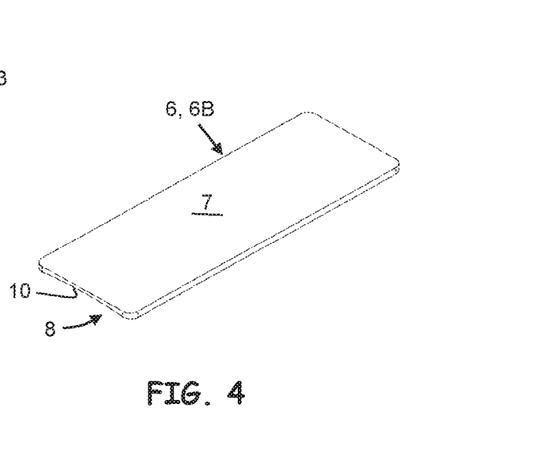
FIG. 4 shows an electrically conductive coupling element for electrically connecting an RFID memory tag to a metal instrument component forming an antenna.

The electrically conductive coupling element 6 shown in FIGS. 3 and 4 comprises a plate-shaped, electrically conductive, in particular metal or metal-comprising shaped element 6B. The shaped element 6B comprises two opposing base surfaces which form the first and second coupling surfaces 7, 8, and a plurality of side surfaces, for example four, which connect the coupling surfaces 7, 8. The first base or coupling surface 7, on which the RFID memory tag 3 is arranged, is planar. The second base or coupling surface 8, which contacts the metal instrument component 2, is bent, especially concave. It can be seen in particular in FIG. 4 that this second bend 10 extends from one of the side faces towards a center line of the second base or coupling face 8, so that the thickness or the wall thickness of the shaped element 6B decreases towards the center line.

FIG. 5 shows a schematic representation of the structure and some components of an RFID memory tag 3, which is electrically connected via an electrically conductive coupling element 6 to a metal, curved instrument component 2 which forms an antenna. The RFID memory tag 3 comprises a carrier 15, especially a ceramic carrier, for the memory chip 4. At least one electrical conductor 16, in particular in the form of an electrically conductive coating, which is electrically connected to the memory chip 4, is provided on the carrier 15 and transfers energy and/or data to the memory chip 4. An electrically insulating protective layer 17, for example in the form of a varnish, surrounds the carrier 15, the memory chip 4, and the electrical conductor 16. The in particular ceramic carrier 15 and the electrical conductor 16 electrically connected to the memory chip 4 in particular form an antenna section of the RFID memory tag 3, which cooperates with the metal instrument component 2, 11 to form an antenna 5 for energy and/or data transfer to the reading and/or writing device.

The first coupling surface 7 of the electrically conductive coupling element 6 in FIG. 5, on which the RFID memory tag 3 is arranged, is planar and comprises two planar surfaces separated by a step. The second base or coupling surface 8 is curved, in particular concave, shaped and contacts the convex curved instrument component 2 forming an antenna.

A cap 18 fastened to the medical or dental instrument 1, in particular to the metal instrument component 2 forming an antenna 5 and/or to the outer shell 11, encloses the RFID memory tag 3 and in particular also the electrically conductive coupling element 6. The cap 18, which is also shown in FIGS. 1-3, is fastened in particular to the metal instrument component 2 such that the RFID memory tag 3 and in particular also the electrically conductive coupling element 6 are enclosed sealingly, in order to prevent the penetration of foreign substances from outside into the RFID memory tag 3.

FIG. 5 additionally schematically indicates that the electrically conductive coupling element 6 with at least parts of the RFID memory tag 3 and the metal instrument component 2 (at least part of the outer shell 11) forming an antenna 5 forms an electrical capacitor 13 for capacitive energy and/or data transfer, in particular in an equivalent circuit. The electrodes of the capacitor 13 are formed in particular by the metal instrument component 2, for example a portion of the outer shell 11, the electrically conductive coupling element 6, and electrically conductive elements of the RFID memory tag 3, for example the electrical conductor 16 electrically connected to memory chip 4, which in particular has an electrically conductive coating. The dielectric of the capacitor 13 comprises in particular the electrically insulating protective layer 17 of the RFID memory tag 3, which preferably surrounds at least the memory chip 4.

In FIG. 6, the RFID memory tag 3 is integrated into the medical or dental instrument 1, in particular into the outer shell 11, so that it preferably protrudes only slightly above the outer shell 11, is flush with the outer shell 11, or is completely accommodated within the outer shell 11. In particular, the RFID memory tag 3 does not protrude as far beyond the outer shell 11 as shown for the medical or dental instrument 1 in FIG. 1. The RFID memory tag 3 is preferably arranged on an electrically insulating component 23 that is attached or can be attached to the medical or dental instrument 1. The electrically insulating component 23, for example, is made of ceramic or plastic to ensure undisturbed energy and/or data transfer. The electrically insulating component 23 comprises, for example, a ring-shaped or curved element which can be pushed onto a component of the medical or dental instrument 1. For example, the ring-shaped or curved component 23 can be pushed over the coupling sleeve 12 of the coupling device 21 and, in particular, fastened to the medical or dental instrument 1 using one or more screws 24.

FIG. 7A shows a possible embodiment of an RFID memory tag 3 integrated into the medical or dental instrument 1, in particular into the outer shell 11. As described with reference to the above embodiments, the metal instrument component 2, which here is formed, for example, by at least a part of the coupling sleeve 12 and/or the outer shell 11, has a first bend 9 and the second coupling surface 8 of the electrically conductive coupling element 6 has a second bend 10 complementary to the first bend 9 of the metal instrument component 2. The first bend 9 and the second bend 10 are interlocked to electrically connect the RFID memory tag 3 to the metal instrument component 2, forming an antenna 5. The electrically conductive coupling element 6 can be designed both as an electrically conductive adhesive 6A or as a shaped element 6B, as described above.

Figure 7B:
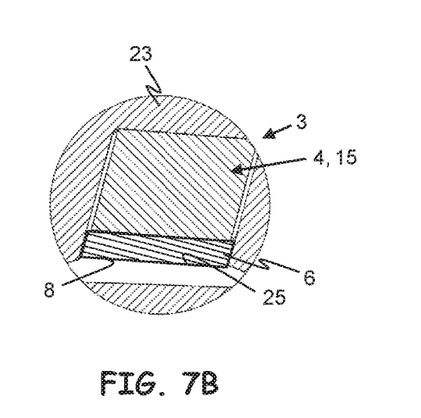
FIG. 7B shows another cross-sectional view of an RFID memory tag arranged on a metal instrument component that forms an antenna for the RFID memory tag.

FIG. 7B shows an alternative embodiment of an RFID memory tag 3 integrated into the medical or dental instrument 1, in particular into the outer shell 11. Here the metal instrument component 2, which for example is formed by at least part of the coupling sleeve 12 and/or the outer shell 11, has a planar surface 25 on which the RFID memory tag 3 is arranged. Accordingly, the second coupling surface 8 of the electrically conductive coupling element 6 is also planar. For the electrical connection of the RFID memory tag 3 to the metal instrument component 2 forming an antenna 5, the planar surface 25 and the planar second coupling surface 8 contact one another. The electrically conductive coupling element 6 can be designed both as an electrically conductive adhesive 6A or as a shaped element 6B, as described above.

The embodiments described or shown, in particular, serve to depict the invention. The characteristics, disclosed in an embodiment, are therefore not limited to that embodiment, but can rather be combined individually or together with one or more characteristics of one of the other embodiments.

What is claimed is:

1. A handheld medical or dental instrument for treatment or diagnosis or driving a tool connectible to the handheld medical or dental instrument, the handheld medical or dental instrument comprising:
   an RFID memory tag having a memory chip for storing data, a carrier which carries the memory chip, and an electrical conductor provided on the carrier that is electrically connected to the memory chip and forms an antenna section of the RFID memory tag;

an electrically conductive coupling element comprising a substantially planar first coupling surface on which the RFID memory tag is arranged and an opposing second coupling surface; and a metal instrument component of the handheld medical or dental instrument to which the RFID memory tag is coupled, wherein metal instrument component is electrically connected to the RFID memory tag via the second coupling surface of the electrically conductive coupling element, and wherein the metal instrument component forms an antenna for the RFID memory tag for wireless energy and/or data transfer to/from a remote reading and/or writing device, wherein the electrically conductive coupling element and at least parts of the RFID memory tag and the metal instrument component form an electrical capacitor for capacitive energy and/or data transfer between the RFID memory tag and the metal instrument component and wherein a dielectric of the electrical capacitor comprises an electrically insulating protective layer which encloses the RFID memory tag.

2. The handheld medical or dental instrument according to claim 1, wherein
the metal instrument component comprises a first bend, and
the second coupling surface of the electrically conductive coupling element comprises a second bend complementary to the first bend of the metal instrument component, wherein
the first bend and the second bend are interlocked to electrically connect the RFID memory tag to the metal instrument component.

3. The handheld medical or dental instrument according to claim 1, wherein
the metal instrument component comprises a metal hollow cylindrical sleeve.

4. The handheld medical or dental instrument according to claim 3, wherein
the metal hollow cylindrical sleeve comprises at least a portion of a grip sleeve or an outer shell.

5. The handheld medical or dental instrument according to claim 1, wherein
electrodes of the electrical capacitor for capacitive energy and/or data transfer are formed by the electrical conductor of the RFID memory tag, the metal instrument component and the electrically conductive coupling element.

6. The handheld medical or dental instrument according to claim 1, wherein
the electrically conductive coupling element comprises an electrically conductive adhesive which affixes and electrically connects the RFID memory tag to the metal instrument component.

7. The handheld medical or dental instrument according to claim 1, wherein
the electrically conductive coupling element comprises a shaped element comprising metal or a carrier material comprising metal particles.

8. The handheld medical or dental instrument according to claim 5, wherein
the metal instrument component is formed by a portion of an outer shell of the handheld medical or dental instrument.

9. The handheld medical or dental instrument according to claim 1, wherein
the electrically conductive coupling element is plate-shaped and comprises at least one curved surface.

10. The handheld medical or dental instrument according to claim 1, wherein
the electrically insulating protective layer which forms a dielectric of the capacitor comprises a varnish.

11. The handheld medical or dental instrument according to claim 1, wherein
the electrically insulating protective layer is arranged between the electrical conductor of the RFID memory tag and the electrically conductive coupling element.

12. The handheld medical or dental instrument according to claim 1, further comprising
a cap which is fastened to the handheld medical or dental instrument and encloses the RFID memory tag.

13. The handheld medical or dental instrument according to claim 12, wherein
in addition the cap encloses the electrically conductive coupling element.

14. A method for manufacturing or retrofitting a handheld medical or dental instrument for treatment or diagnosis or driving a tool connectible to the handheld medical or dental instrument, the method comprising:
providing a handheld medical or dental instrument for treatment or diagnosis or driving a tool connectible to the handheld medical or dental instrument comprising a metal hollow sleeve which holds in its interior a water or air supply line;
providing an RFID memory tag comprising a memory chip for storing data, a carrier which carries the memory chip, and an electrical conductor provided on the carrier that electrically connects to the memory chip and forms an antenna section of the RFID memory tag; and
attaching the RFID memory tag to the outside of the metal hollow sleeve through an electrically conductive coupling element, wherein the RFID memory tag is electrically connected to the metal hollow sleeve, so that the metal hollow sleeve forms an antenna for the RFID memory tag for wireless energy and/or data transfer to/from a remote reading and/or writing device,
wherein the electrically conductive coupling element comprises a substantially planar first coupling surface on which the RFID memory tag is arranged and a second coupling surface arranged on the metal hollow sleeve, and
wherein the electrically conductive coupling element and at least parts of the RFID memory tag and the metal hollow sleeve form an electrical capacitor for capacitive energy and/or data transfer between the RFID memory tag and the metal hollow sleeve.

15. The method for manufacturing or retrofitting a handheld medical or dental instrument, according to claim 14, wherein
the metal hollow sleeve comprises a first bend, and
the second coupling surface of the electrically conductive coupling element comprises a second bend complementary to the first bend of the metal hollow sleeve, wherein
the first bend and the second bend are interlocked to electrically connect the RFID memory tag to the metal hollow sleeve forming an antenna.

16. A medical or dental handpiece, comprising:

a metal hollow cylindrical sleeve;

an RFID memory tag having a memory chip for storing data, wherein the RFID memory tag is attached to the medical or dental handpiece such that the RFID memory tag is electrically connected to the metal hollow cylindrical sleeve such that the metal hollow cylindrical sleeve forms an antenna for the RFID memory tag for wireless energy and/or data transfer to/from a remote reading and/or writing device;

an electrically conductive coupling element formed by an adhesive having electrically conductive particles and arranged at the outside of the metal hollow cylindrical sleeve and electrically connecting the RFID memory tag to the metal hollow cylindrical sleeve forming an antenna, the electrically conductive coupling element comprising a substantially planar first coupling surface on which the RFID memory tag is arranged and a second coupling surface arranged on the metal hollow cylindrical sleeve forming the antenna, and a cap which is fastened to the metal hollow cylindrical sleeve and encloses the RFID memory tag, wherein the electrically conductive coupling element and the cap comprise the same adhesive, but the adhesive forming the cap does not have electrically conductive particles.

17. The medical or dental handpiece according to claim 16, wherein the metal hollow cylindrical sleeve comprises an outer shell having a gripping section to be manually held.

18. The medical or dental handpiece according to claim 16, wherein the metal hollow cylindrical sleeve comprises a bearing sleeve for an element of the medical or dental handpiece.

19. The medical or dental handpiece according to claim 16, wherein the metal hollow cylindrical sleeve comprises a coupling sleeve for the detachably connection of the medical or dental handpiece to a coupling part.

20. The medical or dental handpiece according to claim 16, wherein the medical or dental handpiece comprises a motor unit for driving a tool or a coupling element for connection to a media source or a source of electrical energy.

* * * * *